(12) United States Patent
Bruce

(10) Patent No.: US 6,177,989 B1
(45) Date of Patent: Jan. 23, 2001

(54) LASER INDUCED CURRENT FOR SEMICONDUCTOR DEFECT DETECTION

(75) Inventor: Michael Bruce, Austin, TX (US)

(73) Assignee: Advanced Micro Devices, Sunnyvale, CA (US)

( * ) Notice: Under 35 U.S.C. 154(b), the term of this patent shall be extended for 0 days.

(21) Appl. No.: 09/259,542

(22) Filed: Mar. 1, 1999

(51) Int. Cl.[7] .................................................. G01N 21/00
(52) U.S. Cl. ..................................... 356/237.5; 250/559.4
(58) Field of Search ................................. 250/559.4, 208, 250/206, 559.22; 356/237.2, 237.3, 237.4, 237.5

(56) References Cited

U.S. PATENT DOCUMENTS 6,091,488 * 7/2000 Bishop .............................. 356/237.5

OTHER PUBLICATIONS

Hornguchi, Koshi, Microscopic Optical Beam Induced Current Measurements and Their Applications, *International Measurement and Test Conference*, IMTC 1994, p. 693–699.

Komoda, Hirotaka and Shimizu, Katsusuke, Optical Beam Induced Current Techniques for Failure Analysis of Very Large Scale Integrated Circuits Devices, *Jpn. J. Appl. Phys.*, vol. 33 (1994) p. 3393–3401.

Nishikawa, A., Odani, C., Miura, N, Novel Failure Analysis Technique "Light Induced State Transition (LIST" Method Using an OBIC System, 23rd *International Symposium for Testing and Failure Analysis*, 1997, p. 159–163.

Wilson, Tony and Pester, Paul D., An Analysis of the Photoinduced Current from a Finely Focused Light Beam in Planar p–n Junctions and Schottky–Barrier Diodes, *IEEE Transactions on Electron Devices*, vol. Ed–34, p. 1564–1570.

* cited by examiner

Primary Examiner—Hung Xuan Dang

(57) ABSTRACT

A process and apparatus for analyzing an integrated circuit using laser induced current and photoemissions. A laser source is positioned to scan the integrated circuit with laser light and induce current in nodes of the circuit. Laser light reflected from the integrated circuit is filtered using a laser filter. Photo-emissions from the integrated circuit are detected with a photo-emission detector.

26 Claims, 2 Drawing Sheets

LASER INDUCED CURRENT FOR SEMICONDUCTOR DEFECT DETECTION

FIELD OF THE INVENTION

The invention relates to inspection of integrated circuits, and more particularly to inspecting integrated circuits using laser-induced current.

BACKGROUND OF THE INVENTION

The semiconductor industry has seen tremendous advances in technology in recent years, permitting dramatic increases in circuit density and complexity, and equally dramatic decreases in power consumption and package sizes. Present semiconductor technology now permits single-chip microprocessors with many millions of transistors, operating at speeds of tens (or even hundreds) of MIPS (millions of instructions per second) to be packaged in relatively small, air-cooled semiconductor device packages. A by-product of such high-density and high functionality in semiconductor devices has been the demand for increased numbers of external electrical connections to be present on the exterior of the die and on the exterior of the semiconductor packages which receive the die, for connecting the packaged device to external systems, such as a printed circuit board.

Typically, dies contain a bonding pad which makes the electrical connection to the semiconductor package. To shorten the electrical path to the pad, the bonding pads were moved to the side of the die nearest the transistors and other circuit devices formed in the die. Connection to the package is made when the chip is flipped over and soldered. As a result, the dies are commonly called flip chips in the industry. Each bump on a pad connects to a corresponding package inner lead. The packages which result are lower profile and have lower electrical resistance and a shortened electrical path. The plurality of ball-shaped conductive bump contacts (usually solder, or other similar conductive material) are typically disposed in a rectangular array. The packages are occasionally referred to as "Ball Grid Array" (BGA) or "Area Grid Array" packages.

FIG. 1 is a cross-sectional view of an example BGA device 10. The device 10 includes an integrated circuit 12 mounted upon a larger package substrate 14. Substrate 14 includes two sets of bonding pads: a first set of bonding pads 16 on an upper surface adjacent to integrated circuit 12 and a second set of bonding pads 18 arranged in a two-dimensional array across an underside surface. Integrated circuit 12 includes a semiconductor substrate 20 having multiple electronic components formed within a circuit layer 22 upon a front side surface of semiconductor substrate 20 during wafer fabrication. The back side surface 23 remains exposed after the device 10 is formed. The electronic components are connected by electrically conductive interconnect lines to form an electronic circuit. Multiple I/O pads 24 are also formed within circuit layer 22. I/O pads 24 are typically coated with solder to form solder bumps 26.

The integrated circuit is attached to the package substrate using the controlled collapse chip connection method, which is also known as the C4® or flip-chip method. During the C4 mounting operation, solder bumps 26 are placed in physical contact with corresponding members of the first set of bonding pads 16. Solder bumps 26 are then heated long enough for the solder to reflow. When the solder cools, I/O pads 24 of integrated circuit 12 are electrically and mechanically coupled to the corresponding members of the first set of bonding pads 16 of the package substrate. After integrated circuit 12 is attached to package substrate 14, the region between integrated circuit 12 and package substrate 14 is filled with an under-fill material 28 to encapsulate the C4 connections and provide additional mechanical benefits.

Package substrate 14 includes one or more layers of signal lines that connect respective members of the first set of bonding pads 16 and the second set of bonding pads 18. Members of the second set of bonding pads 18 function as device package terminals and are coated with solder, forming solder balls 30 on the underside surface of package substrate 14. Solder balls 30 allow BGA device 10 to be surface mounted to an ordinary PCB. During PCB assembly, BGA device 10 is attached to the PCB by reflow of solder balls 30 just as the integrated circuit is attached to the package substrate.

The C4 mounting of integrated circuit 12 to package substrate 14 prevents physical access to circuit layer 22 for failure analysis and fault isolation. Thus, new approaches that are efficient and cost-effective are required.

One prior method for analyzing defects in a circuit includes the use of a photo-emission microscope to view a circuit which is powered. Defects within the powered circuit photo-emit, wherein the photo-emissions are recorded with a photo-emission microscope. A drawback to this approach is that the location of the defect must be in a high state prior to examination of a particular region with the photo-emission microscope to be observable. Therefore, an apparatus and method that provides fast and cost effective analysis of semiconductor circuits is desirable.

SUMMARY OF THE INVENTION

In one embodiment, a process is provided for analyzing an integrated circuit using laser induced current and photoemissions. A laser source is positioned to scan the integrated circuit with laser light and induce current in nodes of the circuit. Laser light reflected from the integrated circuit is filtered using a laser filter. Photo-emissions from the integrated circuit are detected with a photo-emission detector.

In another embodiment, a process is provided for analyzing an integrated circuit. The process comprises scanning the integrated circuit with a beam of laser light having sufficient energy to induce a current in nodes of the integrated circuit. The laser light reflected from the integrated circuit is filtered, and a photo-emission generated from the induced current is then detected.

In yet another embodiment, a process for analyzing an electronic circuit comprises scanning the back side surface with a beam of electromagnetic radiation, whereby current is induced in nodes of the circuit; and detecting a photo-emission from the substrate resulting from the induced current in the circuit.

An apparatus is provided for analyzing an electronic circuit formed upon a front side surface of a semiconductor structure having opposed front side and backside surfaces in another embodiment. The apparatus comprises means for producing a beam of laser light; means for scanning the back side surface of the semiconductor structure with the laser light, whereby the laser light induces a current in nodes of circuit; and means for detecting a photo-emission from semiconductor structure resulting from the induced current.

The above summary is not intended to describe each illustrated embodiment or every implementation of the present invention. The figures and the detailed description which follow more particularly exemplify these embodiments.

BRIEF DESCRIPTION OF THE DRAWINGS

The following detailed description of the preferred embodiments can best be understood when read in conjunction with the following drawings, in which.

Figure 1:
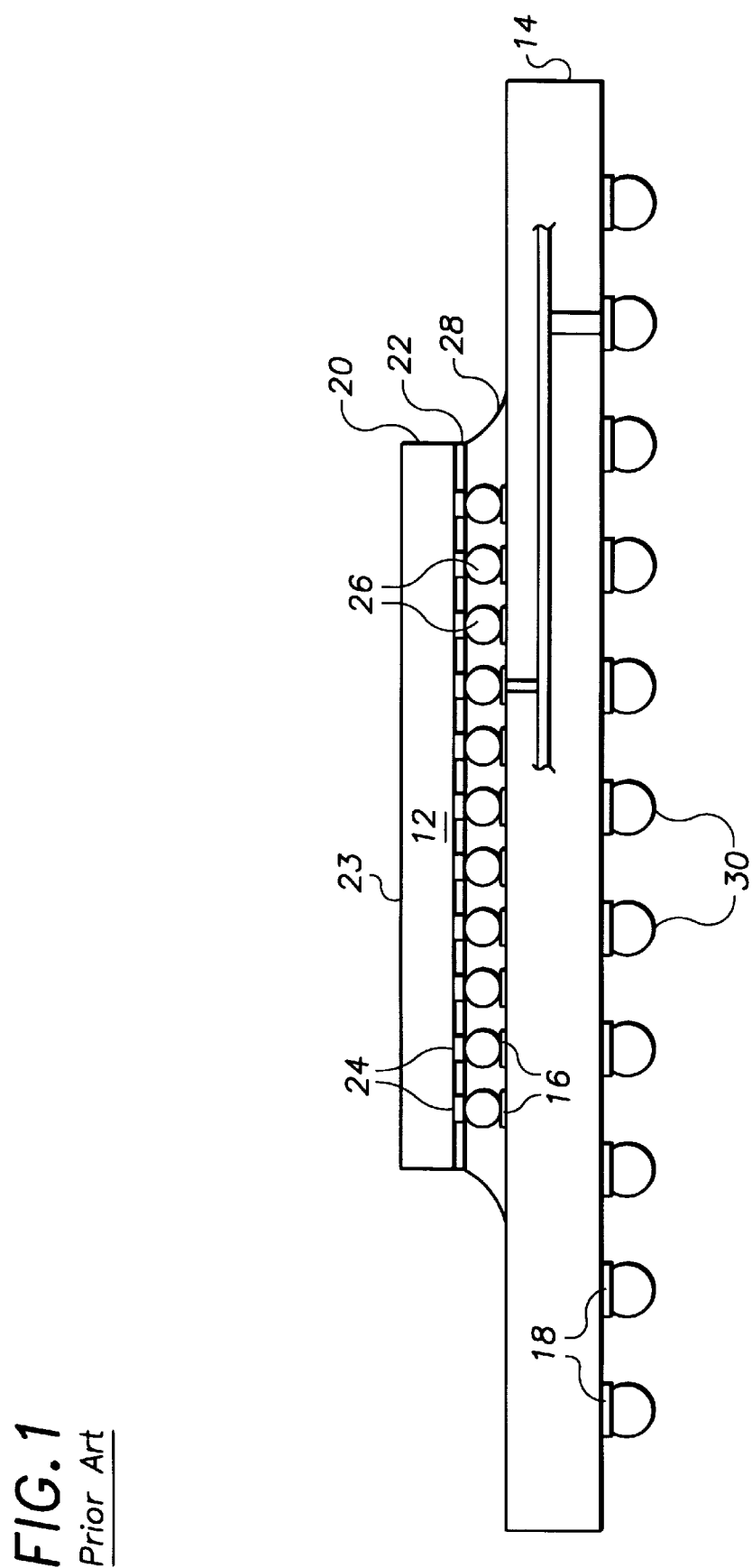
FIG. 1 is a side view of a prior art ball grid array arrangement.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable to a variety of semiconductor structures. The invention has been found to be particularly advantageous in analyzing flip-chip structures. While the present invention is not so limited, an appreciation of various aspects of the invention is best gained through a discussion of the example embodiments set forth below in which a flip-chip is analyzed.

Generally, in the various embodiments of the invention, an integrated circuit is scanned with a beam of laser light. As nodes in the integrated circuit, where a node is a portion of the circuit, are swept with the laser light, the energy from the laser creates electron-hole pairs in the nodes. If there is a defect such as a short circuit, a current is induced in the node and the current causes a photo-emission from the node, which is detected by a photo-emission detector. Laser light that is reflected from the integrated circuit is filtered so as not to interfere with the photo-emission detector. Photo-emissions from the circuit are presented as a computer generated image, which can be either visually inspected or automatically processed to identify specific coordinates on the integrated circuit for further inspection. Further inspection can be performed, for example, by applying power to the circuit and using a photo-emission microscope to inspect the circuit at the identified coordinates. Alternatively, or in addition, various test vectors can be constructed to exercise the circuitry at the identified coordinate.

Figure 2:
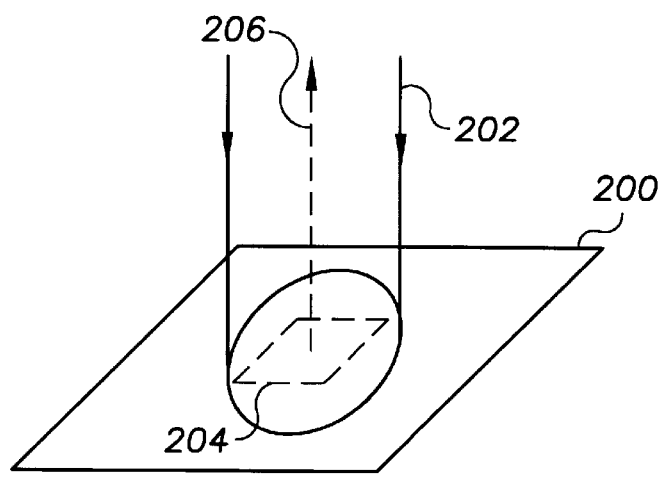
FIG. 2 is a perspective view of a semiconductor structure at which a beam of laser light is directed.

FIG. 2 is a perspective view of a semiconductor structure 200 at which a beam 202 of laser light is directed. The dashed line block 204 is an exaggerated depiction of a node within the integrated circuit. The beam 202 of laser light, also exaggerated in size, illuminates node 204. If the node has a short circuit, a current is induced therein, thereby causing a photo-emission 206. While not shown, it will be appreciated that some portion of the laser light 202 is also reflected from the integrated circuit 200. It is expected that the photo-emission will have a wavelength of 0.9 to 2 $\mu$m for flip chips and will have an intensity that is greatest at about 1.3 $\mu$m.

The coordinates of the photo-emission 206 can be mapped to a region of the integrated circuit 200 in order to ascertain the particular circuitry that comprises the node 204. Once the node has been identified, various test vectors can be constructed and applied to exercise the particular circuitry to confirm the defect.

The invention finds use in inspection of both conventional integrated circuit devices, for example, those having the front side exposed, and in flip-chip devices. For conventional devices, the invention can be used to quickly identify the location of a potential defect by scanning the front side of the integrated circuit. The invention is particularly useful for inspecting flip-chip integrated circuits because in such a circuit the front side is obscured from view. Therefore, conventional techniques for visual inspection of the front side of a flip-chip integrated circuit are difficult, if not impossible without destroying the circuit.

Figure 3:
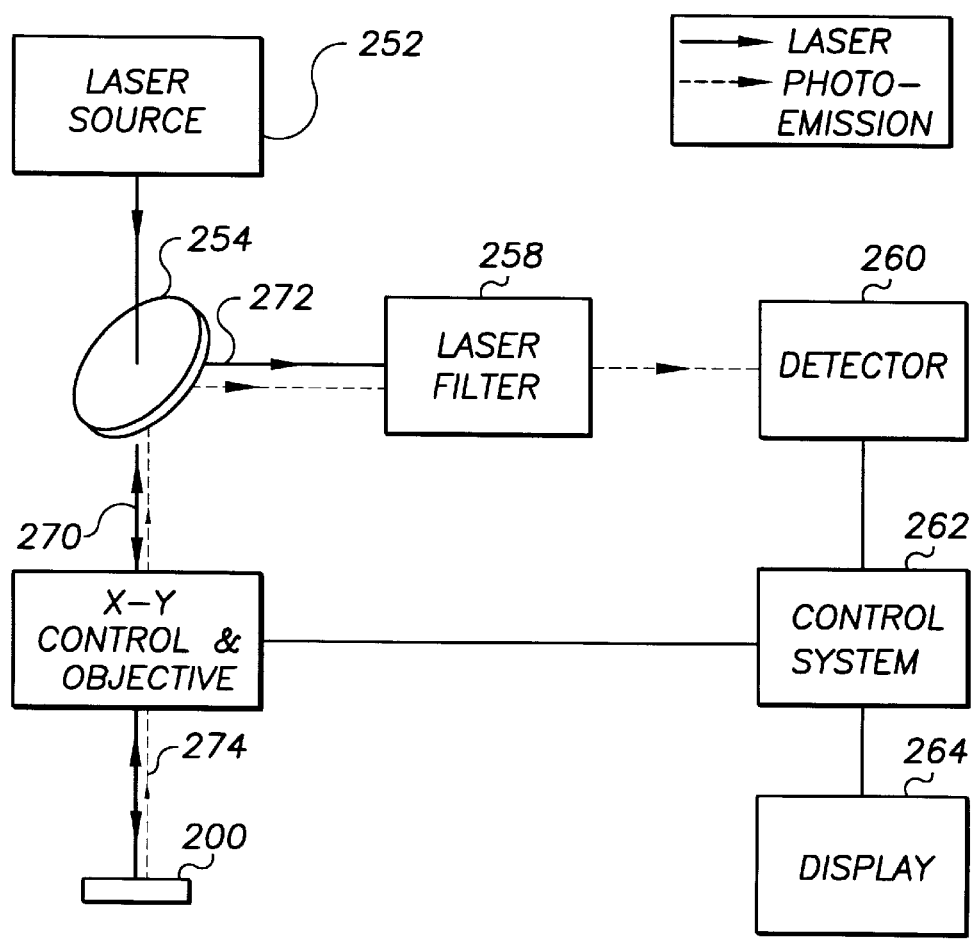
FIG. 3 is a block diagram of an system for inspection of an integrated circuit using laser induced photo-emissions.

FIG. 3 is a block diagram of a system for inspection of an integrated circuit 200 using laser induced photo-emissions. The system includes a laser source 252, a beam splitter 254, scan controller and objective lenses 256, a laser filter 258, a photo-emission detector 260, a control system 262, and a display 264. In operation, the laser source 252 generates a beam of laser light of a selected wavelength. For example, the laser source may be a Model 7910 laser source that is available from Spectra Physics. Wavelengths of between about 900 nm to 1.064 $\mu$m are believed to be suitable. The beam splitter 254 polarizes the laser light, allowing the polarized laser light to pass through as beam 270 and reflecting the laser light that is reflected from the circuit 200 as beam 272. The x-y scan control and objective lenses 256 raster a focused beam of laser light on the circuit 200.

Light produced from photo-emissions in the circuit 200, shown as dashed line 274, is directed to laser filter 258. Laser filter 258 is a narrow band laser light filter, for example, a customized filter can be ordered from CVI Laser Corporation. The pass band of the filter 258 is selected according to the selected wavelength of the laser light provided by the laser source 252, allowing the photo-emitted light 274 to pass and filtering the reflected laser light 272. For example, filter 258 may have a bandwidth of approximately 1050 to 1075 nm. It will be appreciated that more than one filter may be required for intense laser light.

Photo-emission detector 260 produces an image from the photo-emitted light. Suitable devices include, for example, a CCD camera, such as Model CH250 from Photo Metrics or a photo multiplier tube (PMT). The image is provided as input to the control system 262.

The control system is a data processing system that is coupled to the x-y control element 256 and adapted to control the laser scan. The image produced by the detector 260 and displayed on the computer display 264 shows defective areas as areas of relatively intense light. The control system 262 can also be adapted to derive from the coordinates of the photo-emissions depicted in the image the coordinates on the integrated circuit 200 from which photo-emissions are emanating.

As noted above, the present invention is applicable to a number of different semiconductor structures and arrangements. Accordingly, the present invention should not be considered limited to the particular examples described above, but rather should be understood to cover all aspects of the invention as fairly set out in the attached claims. Various modifications, equivalent structures, as well as numerous structures to which the present invention may be applicable will be readily apparent to those of skill in the art upon review of the present specification. The claims are intended to cover such modifications and devices.

What is claimed is:

1. An apparatus for analyzing an integrated circuit, comprising:

a laser source positioned to scan the integrated circuit with laser light and induce current in nodes of the circuit;

a laser filter positioned to collect laser light reflected from the integrated circuit;

a photo-emission detector positioned to receive photo-emissions from the integrated circuit.

2. The apparatus of claim 1, further comprising:

a data processing system coupled to the photo-emission detector, and configured and arranged to generate an image from photo-emissions from the integrated circuit; and a computer display coupled to the data processing system.

3. The apparatus of claim 1, wherein the wavelength of the laser light is between approximately 900 nm and 1.5 µm.

4. The apparatus of claim 1, wherein the filter is a narrow-band laser light filter.

5. The apparatus of claim 4, wherein the bandwidth of the narrow-band filter has a range of approximately 1050 to 1075 nm.

6. The apparatus of claim 1, wherein the photo-emission detector is a photo-diode.

7. The apparatus of claim 1, wherein the photo-emission detector is a CCD camera.

8. The apparatus of claim 1, wherein the photo-emission detector is a photo multiplier tube.

9. A process for analyzing an integrated circuit, comprising the steps of:

scanning the integrated circuit with a beam of laser light having sufficient energy to induce a current in nodes of the integrated circuit;

filtering the laser light reflected from the integrated circuit; and detecting a photo-emission generated from the induced current.

10. The process of claim 9, wherein the integrated circuit forms a semiconductor structure having a front side and a back side, and the back side of the semiconductor structure is laser scanned.

11. The process of claim 9, wherein the integrated circuit forms a semiconductor structure having a front side and a back side, and the front side of the semiconductor structure is laser scanned.

12. The process of claim 9, wherein the wavelength of the laser light is between approximately 900 nm and 1.5 µm.

13. The process of claim 9, further comprising the step of directing the beam of laser light from a diode laser at the integrated circuit.

14. The process of claim 9, further comprising the step of directing the beam of laser light from a YAG laser at the integrated circuit.

15. The process of claim 9, further comprising the step of detecting the photo-emission with a CCD camera.

16. The process of claim 9, further comprising the step of detecting the photo-emission with a photo-diode.

17. The process of claim 9, further comprising the step of mapping a detected photo-emission to a coordinate on the integrated circuit.

18. A process for analyzing an electronic circuit formed upon a front side surface of a semiconductor structure having opposed front side and back side surfaces, comprising:

scanning the back side surface with a beam of electromagnetic radiation, whereby current is induced in nodes of the circuit; and detecting a photo-emission from the substrate resulting from the induced current in the circuit.

19. The process of claim 18, wherein the beam of electromagnetic radiation comprises laser light.

20. The process of claim 19, wherein the wavelength of the laser light is between approximately 900 nm and 1.5 µm.

21. The process of claim 19, further comprising the step of directing the beam of laser light from a diode laser at the integrated circuit.

22. The process of claim 19, further comprising the step of directing the beam of laser light from a YAG laser at the integrated circuit.

23. The process of claim 19, further comprising the step of detecting the photo-emission with a CCD camera.

24. The process of claim 19, further comprising the step of detecting the photo-emission with a photo-diode camera.

25. The process of claim 19, further comprising the step of mapping a detected photo-emission to a coordinate on the integrated circuit.

26. An apparatus for analyzing an electronic circuit formed upon a front side surface of a semiconductor structure having opposed front side and backside surfaces, the apparatus comprising:

means for producing a beam of laser light;

means for scanning the back side surface of the semiconductor structure with the laser light, whereby the laser light induces a current in nodes of circuit; and means for detecting a photo-emission from semiconductor structure resulting from the induced current.

* * * * *

UNITED STATES PATENT AND TRADEMARK OFFICE
CERTIFICATE OF CORRECTION

PATENT NO.    : 6,177,989 B1  
DATED         : January 23, 2001  
INVENTOR(S)   : Bruce It is certified that error appears in the above-identified patent and that said Letters Patent is hereby corrected as shown below:

Title page,
Item [57], ABSTRACT,
Line 2, "photoemissions" should read -- photo-emissions --.

Column 1,
Line 38, "(usually solder, or other" should read -- (usually solder or other --.

Column 2,
Line 31, "using laser induced" should read -- using laser-induced --.
Lines 55-56, "nodes of circuit" should read -- nodes of the circuit --
Line 57, "semiconductor structure" should read -- the semiconductor structure --.

Column 4,
Line 7, "diagram of an system" should read -- diagram of a system --.
Line 8, "using laser induced" should read -- using laser-induced --.

Signed and Sealed this

Fourth Day of February, 2003

JAMES E. ROGAN  
*Director of the United States Patent and Trademark Office*